US010485900B2

(12) United States Patent
Vaz et al.

(10) Patent No.: US 10,485,900 B2
(45) Date of Patent: *Nov. 26, 2019

(54) HPPE MEMBER AND METHOD OF MAKING A HPPE MEMBER

(71) Applicant: DSM IP ASSETS B.V., Heerlen (NL)

(72) Inventors: Claudia Maria Vaz, Echt (NL); Leonardus Gerardus Bernardus Bremer, Echt (NL); Joseph Arnold Paul Maria Simmelink, Echt (NL); Marko Dorschu, Echt (NL); Jozef Maria Rudi Hendrik Goossens, Echt (NL); Harm van der Werff, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 15 days.

This patent is subject to a terminal disclaimer.

(21) Appl. No.: 15/610,190

(22) Filed: May 31, 2017

(65) Prior Publication Data
US 2017/0319753 A1 Nov. 9, 2017

Related U.S. Application Data

(63) Continuation of application No. 13/992,342, filed as application No. PCT/EP2011/072493 on Dec. 12, 2011, now Pat. No. 9,687,593.
(Continued)

(30) Foreign Application Priority Data

Dec. 10, 2010 (EP) .................................. 10194439

(51) Int. Cl.
*A61L 31/04* (2006.01)
*C08L 23/06* (2006.01)
(Continued)

(52) U.S. Cl.
CPC ............. *A61L 31/048* (2013.01); *A61L 27/16* (2013.01); *A61L 29/041* (2013.01); *C08K 3/08* (2013.01);
(Continued)

(58) Field of Classification Search
CPC ...... A61L 27/16; A61L 29/041; A61L 31/048; C08K 3/22; C08K 3/08; C08K 2003/0837;
(Continued)

(56) References Cited

U.S. PATENT DOCUMENTS

| 4,413,110 A | 11/1983 | Kavesh et al. |
| 5,045,072 A | 9/1991 | Castillo et al. |

(Continued)

FOREIGN PATENT DOCUMENTS

| EP | 0200547 | 11/1986 |
| EP | 0205960 | 12/1986 |

(Continued)

OTHER PUBLICATIONS

Honeywell SPECTRA Fiber Datasheet (Year: 2013).*
(Continued)

*Primary Examiner* — Scott R. Walshon
(74) *Attorney, Agent, or Firm* — Nixon & Vanderhye P.C.

(57) ABSTRACT

High performance polyethylene (HPPE) members include at least 5 wt-% of a radiopaque component. The HPPE members are biocompatible and the radiopaque component is a particulate at least partially arranged inside a HPPE filament of the HPPE members. The radiopaque component may have a particle size of at most 1 µm, preferably at most 0.5 µm. Methods of making the HPPE members and various medical devices and repair products which include the HPPE members are also provided.

22 Claims, 4 Drawing Sheets

Related U.S. Application Data (60) Provisional application No. 61/421,714, filed on Dec. 10, 2010.

(51) Int. Cl.
  *A61L 29/04* (2006.01)
  *A61L 27/16* (2006.01)
  *C08K 3/08* (2006.01)
  *C08K 3/22* (2006.01)
  *D01F 11/12* (2006.01)
  *D06M 11/83* (2006.01)
  *D06M 11/47* (2006.01)

(52) U.S. Cl.
  CPC ............... *C08K 3/22* (2013.01); *C08L 23/06* (2013.01); *C08L 2207/062* (2013.01); *D01F 11/123* (2013.01); *D01F 11/127* (2013.01); *D06M 11/47* (2013.01); *D06M 11/83* (2013.01); *Y10T 428/2927* (2015.01)

(58) Field of Classification Search
  CPC ........ D01F 1/123; D01F 11/127; D06M 1/47; D06M 11/83
  See application file for complete search history.

(56) References Cited

U.S. PATENT DOCUMENTS

| | | | |
|---|---|---|---|
| 5,851,668 A | 12/1998 | Sandor | |
| 6,200,338 B1* | 3/2001 | Solomon | A61L 27/18 428/36.9 |
| 6,251,135 B1 | 6/2001 | Stinson et al. | |
| 2010/0329417 A1 | 12/2010 | Abe et al. | |
| 2011/0160661 A1 | 6/2011 | Elton | |

FOREIGN PATENT DOCUMENTS

| | | |
|---|---|---|
| EP | 0213208 | 3/1987 |
| EP | 0472114 | 2/1992 |
| EP | 0504954 | 9/1992 |
| EP | 1445356 | 8/2004 |
| EP | 1627719 | 7/2005 |
| EP | 2 143 387 | 1/2010 |
| GB | 2042414 | 9/1980 |
| JP | 10-52497 | 2/1998 |
| JP | 2007-522351 | 8/2007 |
| JP | 2010-166938 | 8/2010 |
| WO | 01/73173 | 10/2001 |
| WO | 2005/066401 | 7/2005 |
| WO | 2007/003266 | 1/2007 |
| WO | 2007/019874 | 2/2007 |
| WO | 2009/101661 | 8/2009 |
| WO | 2009/115291 | 9/2009 |

OTHER PUBLICATIONS

International Search Report for PCT/EP2011/072493, dated Jan. 17, 2012.
Written Opinion of the International Searching Authority for PCT/EP2011/072493, dated Jan. 17, 2012.
Medel et al; *Comparative Fatigue Behavior and Toughness of Remelted and Annealed Highly Corsslinked Polyethylenes*; Journal of biomedial Materials Research Part B: Applied Biomaterials (2007), vol. 83B, pp. 380-390.

* cited by examiner

HPPE MEMBER AND METHOD OF MAKING A HPPE MEMBER

CROSS-REFERENCE OF THE INVENTION

This application is a continuation of commonly owned U.S. application Ser. No. 13/992,342, filed Nov. 18, 2013 (now U.S. Pat. No. 9,687,593), which is the national phase application under 35 USC § 371 of PCT/EP2011/072493, filed Dec. 12, 2011, which designated the U.S. and claims priority to U.S. Provisional Application No. 61/421,714, filed Dec. 10, 2010 and European Patent Application No. 10194439.5, filed Dec. 10, 2010, the entire contents of each of which are hereby incorporated by reference.

TECHNICAL FIELD OF THE INVENTION

The invention relates to a high performance polyethylene (HPPE) member. More particularly, the invention relates to a radiopaque HPPE member. Furthermore, the invention relates to a method of making a radiopaque HPPE member and applications of a radiopaque HPPE member.

BACKGROUND OF THE INVENTION

High performance polyethylene (HPPE) is widely used in medical devices such as sutures, cables, meshes etc, many of which are used in minimally invasive surgery. There is hence a desire to verify the position of the medical device in applications where visual inspection is not possible during or after surgery. X-rays are commonly used for visualization of other types of medical devices comprising metal parts, however, HPPE absorbs substantially the same amount of x-rays as soft human tissue and HPPE members are traditionally hence not visible using x-ray visualization techniques. Various approaches have been attempted to introduce radiopacity into medical devices comprising HPPE including impregnation with solutions of radiopaque salts such as $BaSO_4$ followed by drying, incorporation of a metal wire in the construction, coating the medical device with a radiopaque coating, and incorporating radiopaque particles of $BaSO_4$ into the yarn. However, these technique leads to one or more of the risk of leaching, reduced flexibility of the yarn, and/or reduced specific strength.

WO 2009/115291 discloses an implant, which may comprise UHMWPE yarn. It is disclosed that the implant also may comprise tantalum metal fiber.

OBJECTS OF THE INVENTION

It is an object of the invention to provide an improved HPPE member.

In another aspect of the invention, it is an object of the invention to provide a method of preparing an improved HPPE member.

In a further aspect of the invention, it is an object of the invention to provide uses of the improved HPPE member.

The improvement may for example be one or more of increased radiopacity combined with substantially the same ultimate tensile strength of the HPPE member; an improved mechanical property of the HPPE member; or another feature of the invention.

DISCLOSURE OF THE INVENTION

One or more of the above and/or other objects of the invention are realised by a high performance polyethylene (HPPE) member, which HPPE member comprises at least 5 wt-% of a radiopaque component, the HPPE member is biocompatible and the radiopaque component is a particulate. The radiopaque component is at least partially arranged inside a HPPE filament of the HPPE member, and the radiopaque component has a particle size of at most 1 µm, preferably the radiopaque component has a particle size of at most 0.5 µm. Surprisingly it was found that the HPPE members possessed a strength of about the same as a HPPE member with the same amount of polyethylene and in other words, that adding the radiopaque component did not deteriorate the performance of the member even at high contents of radiopaque component in HPPE members comprising thin filaments.

In another aspect of the invention, one or more of the above and/or other objects of the invention are realised by a method of manufacturing a HPPE member, which method comprises the steps of
  preparing a mixture of polyethylene in a solvent,
  feeding the mixture to an extruder,
  extruding a polyethylene member into an air gap,
  cooling the polyethylene member in a quench bath,
  stretching the polyethylene filament before, during or after removing at least a part of the solvent from the polyethylene member,
wherein the polyethylene is a UHMWPE, and
a radiopaque particulate component is added into the extruder in an amount of at least 5 wt % of the combination of polyethylene and radiopaque component.

In a further aspect of the invention, one or more of the above and/or other objects of the invention are realised by a medical repair product or implant comprising a HPPE member according to the first aspect of the invention wherein the medical repair product or implant is a medical suture, a medical cable, a laminar wire, a (scoliosis) tether, a (stent) graft, a heart valve, an intervertebral disc, a medical mesh, or a pacing lead. Surprisingly, it was found that the medical repair product according to the invention exhibited substantially the same or similar mechanical properties as a medical device with another type of HPPE member but with the added feature that the medical repair product is radiopaque and that the position of the medical repair product hence may be determined by x-ray.

BRIEF DESCRIPTION OF THE DRAWINGS

The invention will be explained more fully below with reference to exemplary embodiments as well as the figures, in which.

DETAILED DESCRIPTION

By HPPE is herein understood High Performance Polyethylene, which is stretched polyethylene with a Young's modulus (also referred to as E-modulus or just modulus) of at least 30 GPa. HPPE may for example be prepared by a meltspinning process (as for example disclosed in EP1445356), by solid state process (as for example disclosed in EP1627719) or by gelspinning (as for example disclosed in WO 2005/066401). Typically, stretching of the member is required to realize sufficient Young's modulus and/or strength. Preferred types of HPPE are meltspun and gelspun HPPE, which have been stretched to increase the Young's modulus to at least 100 GPa. A particularly preferred type of HPPE is gelspun ultra high molecular weight polyethylene (UHMWPE) yarn with a Young's modulus of at least 100 GPa, as such yarn allows for manufacturing of medical devices with very low profile (e.g. very small size such as cross sectional size of HPPE element, like wall thickness of a catheter or a (stent) graft or diameter of a suture or a cable).

For medical devices, polyethylene members are often prepared by molding or extrusion of (UHMW) polyethylene powder followed by treatment with ionizing radiation to introduce cross linking between polyethylene molecules. This may lead to a tougher member but strongly reduces the strength and stiffness of the member. Typically, the Young's modulus of cross linked polyethylene are below 2 GPa (see for example S. M. Kurtz, The UHMWPE handbook: ultrahigh molecular weight polyethylene in total joint replacement, Academic Press, New York (2009) 2nd edition or Medel, F J; Pena, P; Cegonino, J; Gomez-Barrena, E; Puertolas, J A; Comparative Fatigue Behavior and Toughness of Remelted and Annealed Highly Crosslinked Polyethylenes; Inc. J Biomed Mater Res Part B: Appl Biomater 83B: 380-390, 2007. Cross linked members as for example described in WO 2007/019874 are therefore not relevant in evaluating the present invention. Cross linking is therefore not feasible for HPPE members according to the invention, such as stretched high tenacity polyethylene members, like gel spun UHMWPE members, as the radiation leads to chain scission and due to the stretched molecules disintegration or at least considerable reduction in strength of the member.

The HPPE member according to the invention may be a monofilament, a multifilament yarn, a sheet, a band or a multifilament yarn construction. In a preferred embodiment the HPPE member is a multifilament yarn or a sheet, tape or film, as this allows for manufacturing a wide range of medical repair products, implants and medical devices as described elsewhere herein.

In a highly preferred embodiment, the HPPE member is a HPPE yarn having an ultimate tensile strength of at least 1.5 GPa, more preferably at least 2.5 GPa, more preferably at least 3.0 GPa, more preferably at least 3.5 GPa, and most preferably at least 4.0 GPa. For very high ultimate tensile strength like at least 3.0, 3.5 and 4.0 GPa highly superior medical devices can be obtained, such as sutures, that combine high strength with very small size (diameter) and radiopacity. Ultimate tensile strength, also simply referred to as strength or tenacity of such fibres are determined by known methods based on ASTM D885-85 or D2256-97. There is no reason for an upper limit of tenacity of HPPE fibres, but the fibres typically are of tenacity at most about 5 GPa to 6 GPa. The HPPE members also have a high tensile modulus (also referred to as Young's modulus). It is preferred that the HPPE member has a Young's modulus of at least 70 GPa, preferably at least 100 GPa or at least 125 GPa. HPPE fibres are also sometimes referred to as high-modulus polyethylene fibres.

HPPE fibres can be prepared by spinning of a solution of ultrahigh molecular weight polyethylene (UHMWPE) in a suitable solvent into gel fibres and drawing the fibres before, during and/or after partial or complete removal of the solvent; that is via a so-called gel-spinning process. Gel spinning of a solution of UHMWPE is well known to the skilled person; and is described in numerous publications, including EP 0205960 A, EP 0213208 A1, U.S. Pat. No. 4,413,110, GB 2042414 A, EP 0200547 B1, EP 0472114 B1, WO 01/73173 A1, and in Advanced Fiber Spinning Technology, Ed. T. Nakajima, Woodhead Publ. Ltd (1994), ISBN 1-855-73182-7, and in references cited therein, all incorporated herein by reference.

UHMWPE is understood to be polyethylene having an intrinsic viscosity (IV, as measured on solution in decalin at 135° C.) of at least 5 dl/g, preferably of between about 8 and 40 dl/g. Intrinsic viscosity is a measure for molar mass (also called molecular weight) that can more easily be determined than actual molar mass parameters like $M_n$ and $M_w$. There are several empirical relations between IV and $M_w$, but such relation is dependent on molar mass distribution. Based on the equation $M_w=5.37*10^4 [IV]^{1.37}$ (see EP 0504954 A1) an IV of 8 dl/g would be equivalent to $M_w$ of about 930 kg/mol. Preferably, the UHMWPE is a linear polyethylene with less than one branch per 100 carbon atoms, and preferably less than one branch per 300 carbon atoms; a branch or side chain or chain branch usually containing at least 1 carbon atoms. The linear polyethylene may further contain up to 5 mol % of one or more comonomers, such as alkenes like propylene, butene, pentene, 4-methylpentene or octene.

By radiopaque component is herein meant a substance, which has an X-ray absorbance higher than soft human tissue. Radiopaque components are known in the art and include metals such as for example gold, silver, steel, tantalum, tungsten; salts and bio ceramics such as $BaSO_4$, $Bi_2O_3$, hydroxy apatite, $Ca_3PO_4$, bismuth oxychloride and bismuth subcarbonate. Mixtures of radiopaque components may also be utilized but are not preferred. According to the invention, the radiopaque component is a particulate, which here means that it is a solid not soluble or with a very low solubility in polyethylene and in body fluids below 40° C. Most preferred particulate radiopaque components are tantalum and $Bi_2O_3$. To reduce leaching or other loss of the radiopaque component from the HPPE member, it was found that the radiopaque component should be arranged at least partially inside a HPPE filament of the HPPE member. It could be theorized that this will reduce interaction between the radiopaque component and the body as well as prevent that the x-ray image of the HPPE member will be blurred by migration away from the HPPE member of radiopaque component during use. The particle size of the radiopaque component was found to be highly important for the mechanical properties of the HPPE member. Surprisingly it was found that when the radiopaque component had a particle size of at most 1 μm, then the tensile strength of the HPPE member remained high even for yarn with very thin filaments. Preferably the radiopaque component has a particle size of at most 0.5 μm. The particle size is the diameter of the primary particle established as described elsewhere herein. WO 2009/115291 discloses an implant, which may comprise UHMWPE yarn and a metal fiber, which metal fiber is incorporated into a textile structure. WO 2009/115291 does not disclose or hint to that the metal may be a particulate. A medical implant with a metal fiber is prone to flexfatigue breakage and is hence inferior to a medical implant prepared based on a HPPE member according to the present invention.

By the HPPE member being biocompatible is herein meant that the HPPE member comprises less than 100 ppm organic solvent. Preferably the HPPE member comprises less than 60 ppm organic solvent, and more preferably the HPPE member comprises less than 50 ppm organic solvent. The organic solvent may for example be a solvent used in gelspinning or an additive used during the stretching or cleaning procedure, such as a spin finish or an extrudant.

In a highly preferred embodiment, the HPPE member passes biological testing selected and conducted according to ISO 10993-1: 2009 (Biological evaluation of medical devices—Part 1: Evaluation and testing within a risk management process).

For very small particle size special effects may occur in interaction between the body and the particulate. It was hence found to be an advantage that the radiopaque component has a particle size of at least 0.05 µm, and preferably the particle size is at least 0.075 µm as this reduces the numbers of particles to realize suitable radiopacity of the HPPE member as well as reduces the bioactivity of the particulates. It was found that for particle size above 0.05 µm—and particularly for particle size above 0.075 µm—separation of agglomerates particulates could be readily obtained during mixing step of gel spinning when utilizing $Bi_2O_3$ or tantalum as radiopaque component.

Powders with sub-micron particles are usually agglomerated into larger clusters. It is important that such clusters to a large extent are broken up into the individual particles in order to be able to achieve high concentrations of particles in the HPPE members. This may for example be achieved by use of a stabilizer like OLOA combined with sufficient mechanical action for example by a dissolver disk, grinding or via ultrasonic vibration. Furthermore, it was found that the process of preparing the HPPE member itself (e.g. the mixing and extrusion steps in gelspinning) was also very efficient in separating the agglomerated particles into the primary particles. By particle size is herein meant average particle diameter of the primary particles as measured by a Zetasizer nano after sonication in a sonics vibracell of the radiopaque particulate in decaline with 1% OLOA 1200.

The suitable X-ray linear attenuation coefficient of the HPPE member according to the invention depends on the application of the HPPE member. However, for multifilament yarns it was found to be highly advantageous to have an X-ray linear attenuation coefficient of at least 1 $cm^{-1}$ for 40 keV X-ray radiation, as this allowed to prepare sutures, cables and other constructions, which are radiopaque towards soft tissue without requiring very high thickness of the construction. This will mean that a medical cable of 5 mm diameter would have an x-ray absorbance similar to that of ca. 20 mm soft tissue. More preferred is a multifilament yarns with an X-ray linear attenuation coefficient of at least 5 $cm^{-1}$ for 40 keV X-ray radiation, which corresponds to a content of about 30 wt % $Bi_2O_3$. With this multifilament yarn according to the invention, a medical suture having a diameter of 0.5 mm would have an X-ray absorbance similar to that of ca. 9 mm soft tissue. Even more preferred is a multifilament yarns with an X-ray linear attenuation coefficient of at least 10 $cm^{-1}$ for 50 keV X-ray radiation, which corresponds to a content of about 62 wt % $Bi_2O_3$. With this multifilament yarn according to the invention, a medical suture having a diameter of only 0.1 mm would have an X-ray absorbance similar to that of ca. 2 mm bone.

In a particularly preferred embodiment according to the invention, HPPE member is a multifilament yarn having a filament diameter of less than 18 µm. Preferably, the filament diameter is less than 15 µm and more preferably the filament diameter is less than 12 µm such as less than 9 µm. The smaller diameter allows for more filaments per multifilament yarn for the same size of the multifilament yarn, which was found to be more advantageous in realizing reduced sensitivity to filament breakage and a more even X-ray absorbance. In a preferred embodiment, the filament diameter is at least 5 µm, as thinner filaments require very fine radiopaque particles to prevent substantial reduction of strength as compared to the filament without radiopaque particles. Unless explicitly stated otherwise, by diameter is herein meant the diameter of a circle with the same area as the cross section the filament orthogonal to the length of the filament. The diameter of the filaments is measured by scanning electron microscope.

In general, when the HPPE member is a multifilament yarn, the HPPE member according to the invention may comprise yarns of any linear density, however, multifilament yarns according to the invention are particularly advantageous when the linear density is relatively low. In a preferred embodiment, the linear density of the polyethylene part of the yarn is at most 500 dtex, more preferably at most 120 dtex, more preferably at most 50 dtex. Extreme low linear density of the polyethylene part of the yarn is also feasible such as linear density of the polyethylene part of the yarn below 25 dtex. Since the radiopaque component has a much higher density than the polyethylene part of the yarn, the linear density of such HPPE multifilament yarns including polyethylene and radiopaque component may for example be at most 2000 dtex, more preferably at most 1000 dtex, more preferably at most 500 dtex, such as at most 100 dtex.

In a preferred embodiment, the content of the radiopaque component deviates less than 2% in the length direction of the HPPE member. The deviation in radiopaque component was determined as described in the experimental part below. Such low variation in content of radiopaque component was found to be highly advantageous particularly for surgical repair products or implants prepared from monofilament but also for surgical repair products, implants and medical devices comprising multifilament yarns. More preferably, the content of the radiopaque component deviates less 1% in the length direction of the HPPE member.

Another aspect of the invention concerns a method of manufacturing a HPPE member comprising the steps of preparing a mixture of polyethylene in a solvent. The mixture is preferably homogeneous on a micro or a macro scale, however this is not essential as in most cases the mixing continues in the following processing steps. The solvent may for example be decalin-based or paraffin-based, where decalin-based solvents are preferred as removing of the solvent is easier for such systems.

In addition to solvent and polyethylene, the mixture may also contain additives that are customary for such processes, such as anti-oxidants, thermal stabilizers, antistatics, colorants, etc., up to 15 wt %, preferably 0-10 wt %.

The mixture is then fed to an extruder, such as a double screw extruder, and a polyethylene member is extruded into an air gap, whereafter the polyethylene member is cooled in a quench bath. The polyethylene member is then stretched before, during or after removing at least a part of the solvent from the polyethylene member. The solvent may for example be removed by heating leading to evaporation of the solvent or by extracting with an extraction solvent followed by removal of the extraction solvent.

The type of polyethylene and particularly the molecular weight may vary, but the best results were obtained for UHMWPE as this allows for manufacturing of HPPE exhibiting very high strength. To introduce X-ray absorbance and hence radiopacity, a radiopaque particulate component was added into the extruder (optionally as a component in the mixture comprising polyethylene and solvent) in an amount of at least 5 wt % of the combination of polyethylene and radiopaque component. The amount of radiopaque particulate may be considerably higher than 5 wt %, such as at least 15 wt %, at least 25 wt %, at least 35 wt % or even at least 50 wt %. It was found that the concentration of the radiopaque component preferably should be less than about 80 wt % as the mechanical properties such as ultimate tensile strength, decreased rapidly for higher contents. In one embodiment, the concentration of the radiopaque component is less than about 60 wt %. The content of radiopaque component is measured by thermogravimetry.

The radiopaque component should be a particulate having a particle size of at most 1 µm, and preferably the particle size is at most 0.5 µm the radiopaque as discussed elsewhere herein.

Advantageously, the radiopaque component may have a particle size of at least 0.05 µm, and preferably a particle size is at least 0.075 µm The radiopaque component may be added as (dry) solid powder or as stable mixture of one or more solvents and preferably the one or more solvents is also the solvent for preparation of the mixture of polyethylene and solvent. By stable mixture is here meant that the radiopaque component settles very slowly so that no substantial variation in concentration exists in the mixture within two hours. This may for example be realized by adding a surfactant in which case it is highly preferred that the surfactant is FDA approved to reduce the risk of the surfactant being not biocompatible.

The radiopaque component may be added by feeding to the mixture comprising UHMWPE and solvent or it may be added directly into the extruder. If added directly into the extruder (without first mixing into the mixture of polyethylene and solvent), then it is preferred that the radiopaque component is added as a stable mixture as described above.

In yet another embodiment of the invention, the HPPE member is a sheet, a tape or a film. Such sheets, tapes or films may be for example produced by feeding the (UHMW) PE and a radiopaque component to an extruder, extruding a sheet, a tape or a film at a temperature above the melting point of the PE and drawing the extruded polymeric sheet, tape or film unidirectionally or biaxially. If desired, prior to feeding the PE to the extruder, the PE and the radiopaque component may be mixed with a suitable liquid organic compound such as for example decaline or paraffin, for instance to form a gel, such as is preferably the case when using UHMWPE. Another way for producing such sheets, tapes or films is via a solid state process comprising the steps of calendaring powdered PE and radiopaque component at elevated temperature to form a coherent sheet, tape or film, followed by stretching the sheet, tape or film unidirectionally or biaxially. Sheets, tapes and films are highly suitable for manufacturing of medical repair products or implants such as for example stent grafts and (heart) valves.

In another embodiment of the invention, the HPPE member tape or film is a porous membrane.

Another aspect of the invention concerns a medical repair product or implant comprising a HPPE member according to the first aspect of the invention. The medical repair product or implant is preferably a medical suture, a medical cable, a laminar wire, a (scoliosis) tether, a (stent) graft, a heart valve, an intervertebral disc, a distal/embolic protection device, a medical mesh or a pacing lead. For these applications there is a high desire for a high strength member which also exhibits high X-ray absorbance.

In a preferred embodiment, the medical repair product or implant comprises at least 50 weight-% HPPE members and preferably HPPE members according to the first aspect of the invention. In another preferred embodiment, the elongated medical repair product or implant comprises at least 80 weight-% HPPE members and most preferably the elongated medical repair product or implant comprises at least 90 weight-% HPPE members. The rest of the medical repair product or implant may for example be another polymer, a metal (for example a needle or an (electrical) cable or a wire) or a coating.

In one embodiment, the medical repair product or implant consists of HPPE members according to the invention. Such medical repair products may for example be orthopaedic sutures or cables.

A preferred embodiment concerns a medical repair product that is an elongated medical repair product. Highly preferred examples of elongated medical repair products are medical sutures and medical cable (for example for orthopaedic or cardio vascular applications), laminar wires, (scoliosis) tether, (stent) grafts, and a pacing lead.

It was found to be highly advantageous that at least a part of the medical repair product or implant has an X-ray linear attenuation coefficient of at least 1 $cm^{-1}$ at 40 keV X-ray radiation, and preferably at least 5 $cm^{-1}$ at 40 keV X-ray radiation, as this allows for the medical repair product or implant to be observable on an X-ray image.

A further aspect of the invention concerns a medical device comprising a HPPE member according to the first aspect of the invention. Preferred examples of such medical devices are medicals balloons, (balloon) catheter, pacing leads, distal/embolic protection devices and textile such as operation gloves and (radiation) protective garment.

The medical devices (as well as medical repair products and implants) according to the invention may consist of or consist substantially of the HPPE member according to the invention, such as forming more than 95 wt % the product. However, in another highly advantageous embodiment, the HPPE member according to the invention only forms a minor part of the medical devices, medical repair products or implants (such as for example less than 10 wt % of the product) for example as X-ray marker whereas other parts of the medical devices, medical repair products or implants may be formed by other materials including for example non-radiopaque HPPE. In such cases, it should be observed that even a small amount of HPPE member according to the invention forms an essential feature of the final medical device, medical repair product or implant in that the HPPE according to the invention provides a differentiating or even qualifying feature of the product.

It should be observed that regarding protective garment and to some extent operation gloves it may not be required that the HPPE member is medical grade as in many cases, smaller traces of solvent and/or spin finish may be acceptable for non-implant applications. Such textiles may for example be highly advantageous for surgeons having to work under X-ray during procedure or for personnel working permanently with X-ray equipment.

In a preferred embodiment, the invention concerns a textile construction comprising a HPPE yarn according to the invention and the textile construction contains no metal fiber.

EXAMPLES

Example 1-4: Preparation of HPPE Members

A suspension of radiopaque component (bismuth-trioxide, Sigma-Aldrich, <100 nm) in decalin was prepared containing 50 wt % $Bi_2O_3$. Particle size of the radiopaque component was measured using a Zetasizer nano after sonication in a sonics vibracell of the radiopaque particulate in decaline with 1% OLOA 1200 to be 0.082 µm. Different amounts of the suspension of radiopaque component was added to a slurry containing decalin, UHMWPE powder, and mixed. The resulting mixtures contained 2, 10, 30 and 50 wt % of $Bi_2O_3$ with respect to total solid weight (i.e. UHMWPE and radiopaque particulate), respectively.

The mixtures were fed to a twin screw extruder. In the extruder the UHMWPE was dissolved in the decalin and the so obtained mixture of the UHMWPE dissolved in the decalin and homogeneously distributed $Bi_2O_3$ was extruded through a spin plate into and air gap, and cooled in a quench bath. Thereafter the solvent was removed during multistage stretching of the yarn whereby HPPE members according to the invention was obtained. The content of decalin in the HPPE multifilament yarns after manufacturing was 40-60 ppm.

The content of radiopaque component was thereafter measured by thermogravimetry. Results are presented in Table 1.

TABLE 1

Content of radiopaque component in HPPE members.

| Experiment | 1 | 2 | 3 | 4a* | 4b* |
|---|---|---|---|---|---|
| $Bi_2O_3$ content [wt %] | 2.2 | 3.3 | 7.5 | 18.5 | 20.6 |
| Linear attenuation coefficient 40 keV (estimated) | 0.29 | 0.44 | 1.05 | 2.9 | 3.3 |
| Linear attenuation coefficient 50 keV (estimated) | 0.16 | 0.25 | 0.59 | 1.62 | 1.85 |

*A number of bobbins were prepared for starting amount of 50 wt % $Bi_2O_3$. Experiment 4a was the one before the last bobbin and experiment 4b was the last bobbin with this starting amount of $Bi_2O_3$.

It is observed that in the content of $Bi_2O_3$ (radiopaque component) was considerably smaller than the theoretical content—particularly for high concentrations of $Bi_2O_3$. It was later discovered that some settlement of $Bi_2O_3$ had occurred during mixing. Only a small part of each batch of mixture was used in the spinning experiment, and despite the large difference between theoretical content and practical content of radiopaque component it was found that the practical content was very stable along the length direction of the final HPPE member as investigated below in Example 8.

Comparative Example 5: Preparation of a HPPE Member without Radiopaque Component A slurry containing decalin, UHMWPE powder and a surfactant was mixed. The resulting mixture was fed to a twin screw extruder. In the extruder the UHMWPE was dissolved in the decalin and the so obtained mixture of the UHMWPE dissolved in the decalin was extruded through a spin plate into and air gap, and cooled in a quench bath. Thereafter the solvent was removed during multistage stretching of the yarn whereby HPPE members without radiopaque component was obtained.

Example 6: Mechanical Properties

Ultimate tensile strength, Young's modulus and elongation-at-break were measured by a procedure derived from ASTM D 885, ASTM D 2256 and ISO 2062 and optimized for HPPE yarns. A gauge length of the yarn of 500 mm was used, a pre-tension (in Newton) of 0.2% of the yarn linear density (in dtex), a crosshead speed of half the gauge length per minute and pneumatic yarn grips from the Instron type CP103684 with Instron 1498K stainless steel faces.

On the basis of the measured stress-strain curve the modulus is determined as the gradient between 0.3 and 1% strain. For calculation of the modulus and strength, the tensile forces measured are divided by the yarn linear density, as determined by ASTM D 1907. Values in GPa are calculated assuming a density of 0.97 $g/cm^3$ for UHMWPE and 8.9 $g/cm^3$ for $Bi_2O_3$. Results are presented in Table 2.

TABLE 2

Mechanical properties.

| Experiment | 1 | 2 | 3 | 4a | 4b | Comp 5 |
|---|---|---|---|---|---|---|
| Radiopaque component [wt %] | 2.2 | 3.3 | 7.5 | 18.5 | 20.6 | 0 |
| Ultimate tensile strength [GPa] | 3.85 | 3.8 | 3.8 | 3.9 | 3.9 | 4.2 |
| Young's modulus [GPa] | 140 | 140 | 130 | 142 | 142 | 148 |
| Elongation-at-break [%] | 3.3 | 3.3 | 3.4 | 3.2 | 3.2 | 3.5 |

Example 7: Deviation in Radiopaque Component

The deviation in radiopaque component was determined by measuring the content of radiopaque component by thermogravimetry for four samples of 1 g, where the samples were sampled with 100 m distance in the length direction of the HPPE member. Thermo gravimetric analysis was done by heating the yarns under helium at 20° C./min up to 800° C. and determining the residual weight, corresponding to the $Bi_2O_3$ mass in the yarn. Thereafter the mean content of radiopaque component was calculated and the deviation for each sample to the mean content was calculated as a percentage of the mean content.

TABLE 3

Measurement of deviation in radiopaque component

| Sample # | Content of radiopaque component [wt %] | Deviation from mean content |
|---|---|---|
| 1 | 18.35 ± 0.33 | 0.8% |
| 2 | 18.59 ± 0.15 | 0.5% |
| 3 | 18.49 ± 0.46 | 0% |
| 4 | 18.53 ± 0.29 | 0.2% |
| Mean | 18.49 | |

Example 8: Distribution of Radiopaque Component in Cross Section

Figure 1:
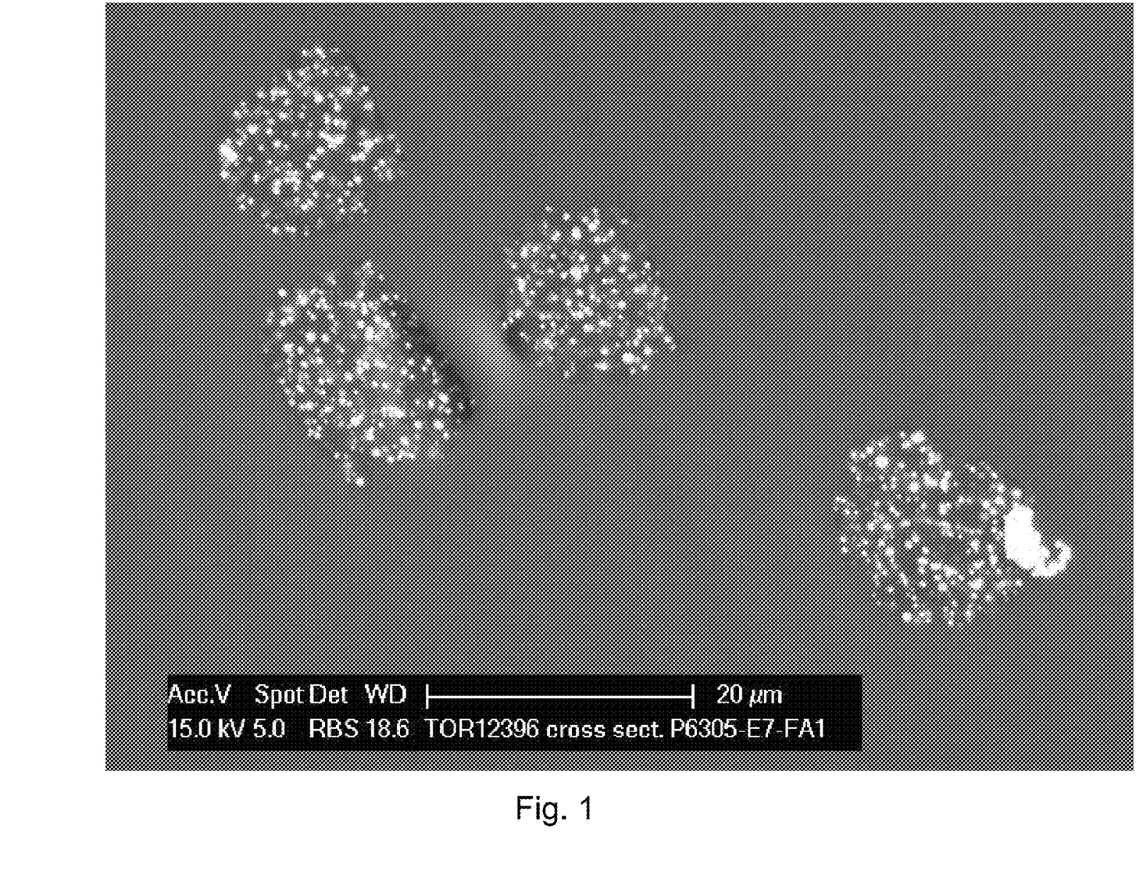
FIG. 1 shows a SEM micrograph of a cross section of a filament according to the invention.
Figure 2:
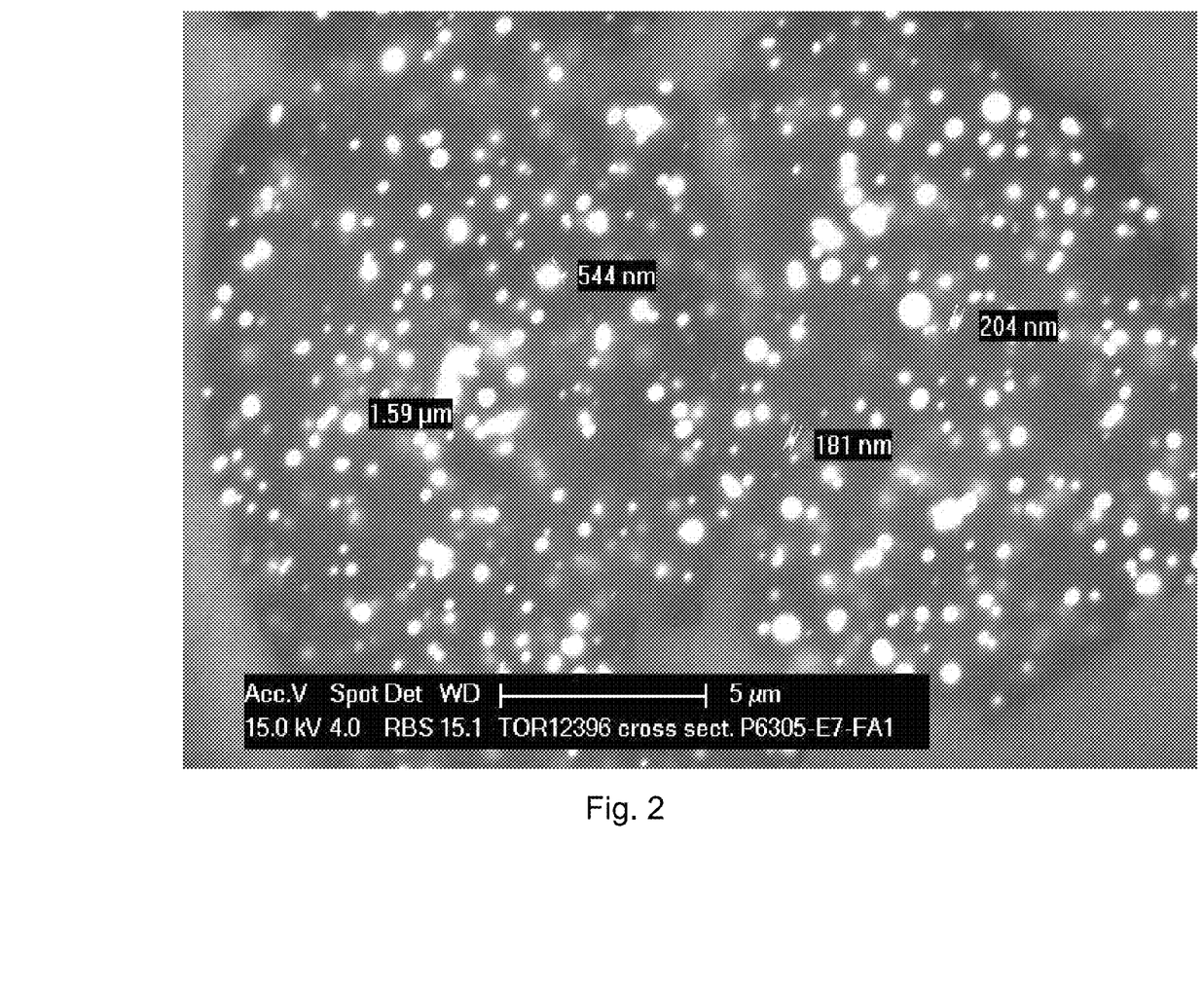
FIG. 2 shows another SEM micrograph of a cross section of a filament according to the invention.
Figure 3:
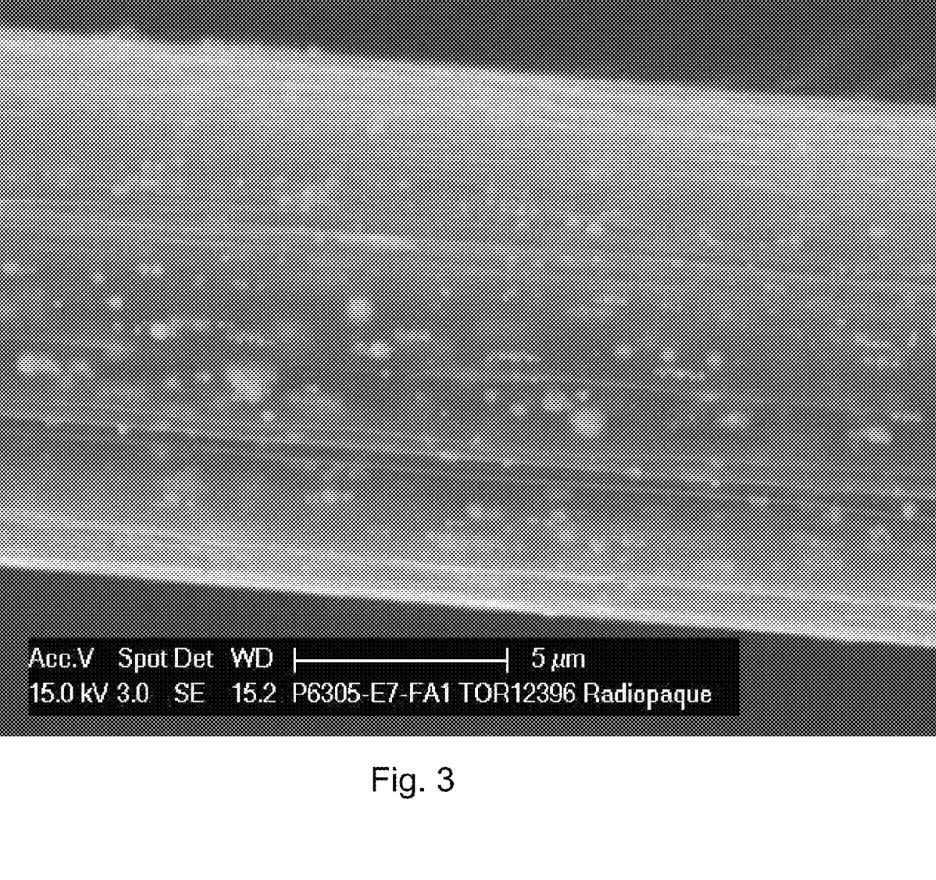
FIG. 3 shows a SEM micrograph of a filament according to the invention seen from the side.

The microscopic distribution of radiopaque component in a cross section of the HPPE member was investigated by scanning electron microscopy. In FIG. 1, cross sections of four filaments of a multifilament yarn are observed. The radiopaque component (here $Bi_2O_3$) is observed as a light spots. In FIG. 2 an enlarged image of another filament is shown. It is observed that the radiopaque component mainly is evenly distributed inside the filament as individual particles separated by and fully enclosed in the dark (almost not scattering) colored polyethylene phase. In FIG. 3 a view of a similar filament seen from the side is shown. Also here, it is observed that the radiopaque component is distributed in throughout the filament lengthwise and cross sectional. It should be noticed that the backscatter technique used here only has limited sensitive to depth and hence backscatter from the radiopaque particles inside the filament will also be observed. This is also observed when comparing FIG. 1, FIG. 2 and FIG. 3. This is highly desirable, as it reduces interaction between the radiopaque component and the body as well as prevents the radiopaque component from migrating from the HPPE member during use, which would increase contact with the body and could introduce a blurring of x-ray images or even decrease total x-ray absorbance over time for images of a medical repair product, implant or medical device comprising the HPPE according to the invention.

Example 9a and 9B: Leaching Experiment

Leaching of $Bi_2O_3$ from multifilament yarns according to the invention was investigated by winding the multifilament yarn of Example 4b on a stick and submersing the multifilament yarn in a test fluid. Thereafter the test fluid was stirred at 600 rpm for 72 h at 50° C., and the concentration of Bi was established with ICP-MS (Inductively Coupled Plasma Mass Spectrometry). Two types of test fluid were applied, namely Cottonseed oil and saline.

TABLE 4

Leaching experiments

| | Experiment 9A | Experiment 9B |
| --- | --- | --- |
| Test fluid | Cottonseed oil | Saline |
| Amount test fluid | 28.73 g | 27.26 g |
| Amount HPPE | 0.2511 g | 0.2568 g |
| Concentration of HPPE in test fluid | 0.01 g/ml | 0.0087 g/ml |
| Concentration of Bi | 7 ppm | <0.2 ppm |

This result of Table 4 clearly indicate that leaching is very limited from the HPPE member in both test fluids.

Example 10: Radiopaque Performance

Radiopacity was measured on a Siemens Axiom Aristos FX Plus at 50 kV, 2.5 mAs. The multi sample piece had a range of HPPE members from single multifilament yarn (sample 4) and constructions of multifilament yarns twisted together of increasing linear density.

Sample 1 (not visible) is the yarn of Experiment 1 (2.2 wt % $Bi_2O_3$) having a linear density of 110 dtex.

Sample 4 is a single multifilament yarn of Experiment 4 (20.6 wt % $Bi_2O_3$) having a linear density of 110 dtex.

Sample 6-1 is two multifilament yarns of Experiment 3 (7.5 wt % $Bi_2O_3$) each having a linear density of 110 dtex.

Sample 6-2 is two multifilament yarns of Experiment 4 (20.6 wt % $Bi_2O_3$) each having a linear density of 110 dtex.

Sample 7-1 (not visible) is a construction of four multifilament yarns of Experiment 1 (2.2 wt % $Bi_2O_3$) each having a linear density of 110 dtex.

Sample 7-2 (not visible) is construction of four multifilament yarns of Experiment 2 (3.3 wt % $Bi_2O_3$) each having a linear density of 110 dtex.

Sample 8-1 (not visible) is a construction of four multifilament yarns of Experiment 3 (7.5 wt % $Bi_2O_3$) each having a linear density of 110 dtex.

Sample 8-2 (not visible) is construction of four multifilament yarns of Experiment 4 (20.6 wt % $Bi_2O_3$) each having a linear density of 110 dtex.

Sample 9-1 is a construction of eight multifilament yarns of Experiment 1 (2.2 wt % $Bi_2O_3$) each having a linear density of 110 dtex.

Sample 9-2 is construction of eight multifilament yarns of Experiment 2 (3.3 wt % $Bi_2O_3$) each having a linear density of 110 dtex.

Sample 10-1 is a construction of eight multifilament yarns of Experiment 3 (7.5 wt % $Bi_2O_3$) each having a linear density of 110 dtex.

Sample 10-2 is construction of eight multifilament yarns of Experiment 4 (20.6 wt % $Bi_2O_3$) each having a linear density of 110 dtex.

Sample 11-1 is a construction of sixteen multifilament yarns of Experiment 1 (2.2 wt % $Bi_2O_3$) each having a linear density of 110 dtex.

Sample 11-2 is construction of sixteen multifilament yarns of Experiment 2 (3.3 wt % $Bi_2O_3$) each having a linear density of 110 dtex.

Sample 12-1 is a construction of sixteen multifilament yarns of Experiment 3 (7.5 wt % $Bi_2O_3$) each having a linear density of 110 dtex.

Sample 12-2 is construction of sixteen multifilament yarns of Experiment 4 (20.6 wt % $Bi_2O_3$) each having a linear density of 110 dtex.

Figure 4:
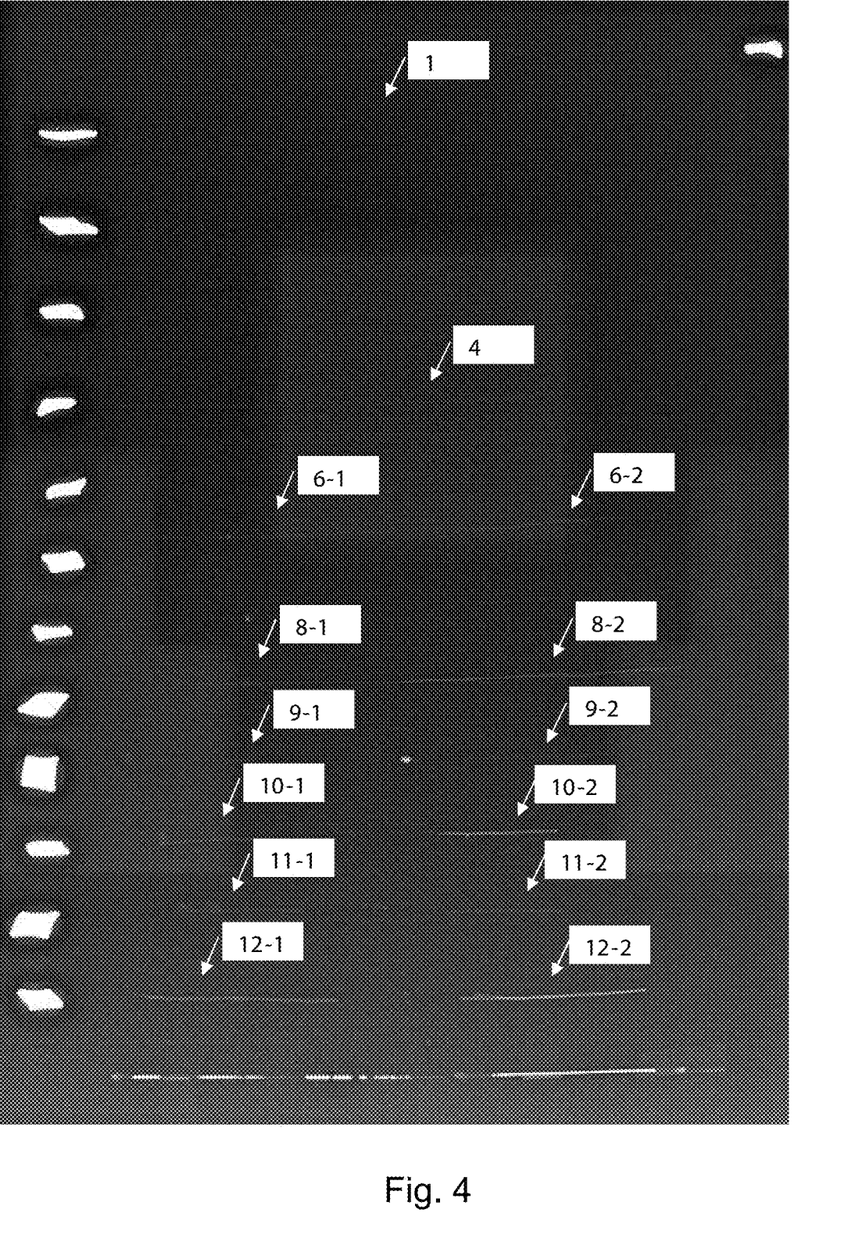
FIG. 4 shows a radiographic image of various sutures.

In FIG. 4, the radiograph is shown. It is observed that even very thin yarns and yarn constructions, are identifiable on the radiograph.

Example 11-16: Preparation of HPPE Members

A radiopaque component ($BaSO_4$, Sachtleben nano, primary particle size 50-100 nm) was utilized. Different amounts of the radiopaque component was added to a slurry containing decalin, UHMWPE powder, and mixed. The resulting mixtures contained 0, 10, 20 and 30 wt % of $BaSO_4$ with respect to total solid weight (i.e. UHMWPE and radiopaque particulate), respectively.

The mixtures were fed to a twin screw extruder. In the extruder the UHMWPE was dissolved in the decalin and the so obtained mixture of the UHMWPE dissolved in the decalin and $BaSO_4$ was extruded through a spin plate into an air gap, and cooled in a quench bath. Thereafter the solvent was removed during multistage stretching of the yarn.

Varying stretch forces during stretching indicated that $BaSO_4$ was not homogenously distributed along the yarn. The concentration was low at the beginning and higher towards the end of the spinning period at any concentration. The resulting yarn did not feel smooth and seemed to contain large clumps of $BaSO_4$.

Example 17: Mechanical Properties

Ultimate tensile strength, Young's modulus and elongation-at-break were measured by a procedure derived from ASTM D 885, ASTM D 2256 and ISO 2062 and optimized for HPPE yarns. A gauge length of the yarn of 500 mm was used, a pre-tension (in Newton) of 0.2% of the yarn linear density (in dtex), a crosshead speed of half the gauge length per minute and pneumatic yarn grips from the Instron type CP103684 with Instron 1498K stainless steel faces.

On the basis of the measured stress-strain curve the modulus is determined as the gradient between 0.3 and 1% strain. For calculation of the modulus and strength, the tensile forces measured are divided by the yarn linear density, as determined by ASTM D 1907. Results are presented in Table 5.

TABLE 5

Mechanical properties

| Experiment | 11 | 12 | 13 | 14 | 15 | 16 |
|---|---|---|---|---|---|---|
| Radiopaque component [wt %] | 0 | 10 (start) | 10 (end) | 20 | 30 (Start) | 30 (high) |
| Ultimate tensile strength [cN/dtex] | 28.9 | 24.3 | 17.7 | 16.5 | 17.3 | Broke* |
| Young's modulus [cN/dtex] | 1089 | 802 | 499 | 437 | 469 | Broke* |
| Elongation-at-break [%] | 2.8 | 3.2 | 3.1 | 3.3 | 2.9 | Broke* |

*It was not possible to perform the final stretch step of sample 16 without breaking the yarn.

The content appeared to vary considerably within each sample and agglomerates of $BaSO_4$ seemed to be present particularly in yarns with higher contents of $BaSO_4$.

Radiopacity of yarns of Examples 11-16 were investigated and the radiopacity appeared to be much lower than the radiopacity of Samples comprising $Bi_2O_3$.

An individual feature or combination of features from an embodiment of the invention described herein, as well as obvious variations thereof, are combinable with or exchangeable for features of the other embodiments described herein, unless the person skilled in the art would immediately realize that the resulting embodiment is not physically feasible.

The invention claimed is:

1. A high-performance polyethylene (HPPE) multifilament yarn comprising at least one HPPE filament, wherein the yarn has a Young's modulus of at least 30 GPa, an ultimate tensile strength of at least 1.5 GPa, is biocompatible, and comprises at least 25 wt % and less than 60 wt % of a particulate radiopaque component having a particle size of at least 0.05 µm and at most 1 µm, and wherein the radiopaque component is at least partially arranged inside the at least one HPPE filament.

2. The HPPE yarn according to claim 1, wherein the HPPE yarn has an ultimate tensile strength of at least 2.5 GPa.

3. The HPPE yarn according to claim 2, wherein the ultimate tensile strength is at least 3.0 GPa.

4. The HPPE yarn according to claim 1, comprising at least 35 wt % of the radiopaque component.

5. The HPPE yarn according to claim 1, wherein the radiopaque component has a particle size of at most 0.5 µm.

6. The HPPE yarn according to claim 1, wherein the radiopaque component is $Bi_2O_3$ or tantalum.

7. The HPPE yarn according to claim 1, wherein the radiopaque component is $Bi_2O_3$.

8. The HPPE yarn according to claim 1, wherein the yarn has a linear attenuation coefficient of at least 1 cm-1 at 40 keV X-ray radiation.

9. The HPPE yarn according to claim 1, wherein the linear attenuation coefficient is at least 5 cm-1 at 40 keV X-ray radiation.

10. The HPPE yarn according to claim 1, wherein radiopaque component content variation is less than 2 wt % in a length direction of the HPPE yarn.

11. The HPPE yarn according to claim 1, wherein the yarn has a linear density of at most 2000 dtex.

12. The HPPE yarn according to claim 1, wherein the at least one HPPE filament has a diameter of less than 18 µm.

13. The HPPE yarn according to claim 1, wherein the at least one HPPE filament has a diameter of at least 5 µm and less than 15 µm.

14. A method of manufacturing the HPPE yarn according to claim 1, the method comprising steps of:
  (a) preparing a mixture of UHMWPE in a solvent,
  (b) feeding the mixture to an extruder,
  (c) adding the particulate radiopaque component to the extruder in an amount of at least 25 wt % and less than 60 wt % based on total weight of the UHMWPE and the radiopaque component,
  (d) extruding the at least one HPPE filament into an air gap,
  (e) cooling the at least one HPPE filament in a quench bath, and
  (f) stretching the at least one HPPE filament before, during or after removing at least a part of the solvent therefrom.

15. The method according to claim 14, wherein the radiopaque component is added to the extruder as a solid or as a stable mixture comprising one or more solvents.

16. A medical repair product or implant comprising a HPPE yarn according to claim 1.

17. The medical repair product or implant according to claim 16, wherein the medical repair product or implant is a medical suture, a medical cable, a laminar wire, a tether, a graft, a heart valve, an intervertebral disc, a distal/embolic protection device, a medical mesh or a pacing lead.

18. The medical repair product or implant according to claim 16, wherein the medical repair product or implant comprises at least 50 wt % of HPPE yarn.

19. The medical repair product or implant according to claim 16, wherein the medical repair product or implant comprises at least 80 wt % of HPPE yarn.

20. The medical repair product or implant according to claim 16, wherein at least a part of the medical repair product or implant has an X-ray linear attenuation coefficient of at least 1 cm-1 at 40 keV X-ray radiation.

21. A medical device comprising a HPPE yarn according to claim 1.

22. The medical device according to claim 21, wherein the medical device is a medical balloon, a catheter, a pacing lead, a distal/embolic protection device, or an operation glove or a protective garment.

* * * * *